United States Patent [19]

Höchstetter

[11] Patent Number: 5,097,027
[45] Date of Patent: Mar. 17, 1992

[54] HETEROCYCLIC COMPOUNDS

[75] Inventor: Hans Höchstetter, Duesseldorf, Fed. Rep. of Germany

[73] Assignee: Bayer Aktiengesellschaft, Leverkusen, Fed. Rep. of Germany

[21] Appl. No.: 593,460

[22] Filed: Oct. 5, 1990

[30] Foreign Application Priority Data

Nov. 11, 1989 [DE] Fed. Rep. of Germany ....... 3937633

[51] Int. Cl.$^5$ .................. C07D 221/22; C07D 223/00
[52] U.S. Cl. ..................... 540/484; 540/553;
540/596; 540/597; 540/599; 544/2; 544/8;
544/11; 544/49; 544/63; 544/65; 544/66;
544/72; 544/73; 544/180; 544/224; 546/37;
546/48
[58] Field of Search ............. 546/37, 48; 540/597,
540/599, 596, 484, 553; 544/2, 8, 11, 49, 63, 65,
66, 72, 73, 180, 224; 106/497, 498, 23

[56] References Cited

U.S. PATENT DOCUMENTS 3,647,798  3/1972  Klein ...................... 546/37
4,714,666 12/1987  Wiedemann et al. ........... 546/37
4,769,460  9/1988  Spietschka et al. .......... 546/37

Primary Examiner—C. Warren Ivy
Assistant Examiner—Raymond Covington
Attorney, Agent, or Firm—Sprung Horn Kramer & Woods

[57] ABSTRACT

Heterocyclic compounds of the formula

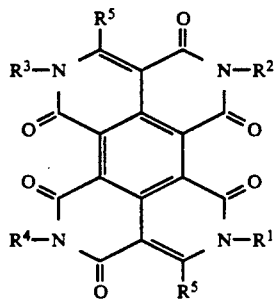

(Ia)

and

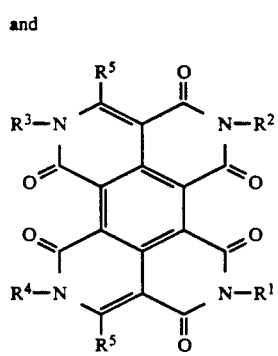

(Ib)

are used as pigments for surface coatings and for coloring and pigmenting high molecular weight organic material.

5 Claims, No Drawings

HETEROCYCLIC COMPOUNDS

The invention relates to heterocyclic compounds of the formula

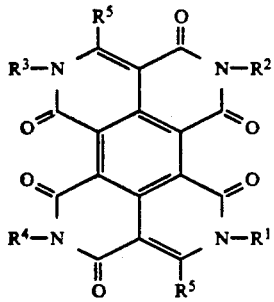

(Ia)

and

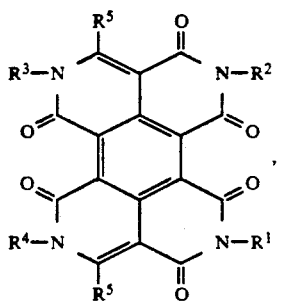

(Ib)

processes for their preparation and their use as dyestuffs or pigments, in particular for colouring or pigmenting high molecular weight organic material, or as pigments for surface coatings, wherein $R^1$, $R^2$, $R^3$ and $R^4$ denote H, alkyl, cycloalkyl, aralkyl, aryl or hetaryl, $R^5$ denotes halogen, $NR^1R^2$, $SR^1$, $OR^1$, aryl, hetaryl or OCat, wherein Cat=a cation, and wherein, for $R^1$ to $R^4$=H, $R^5$ does not represent OH or ONa.

The radicals $R^1$, $R^2$, $R^3$ and $R^4$ can be identical or different. The alkyl, aralkyl, cycloalkyl, aryl and hetaryl radicals can carry substituents. Halogen is preferably F, Cl, or Br. Alkyl represents, for example, $C_1$-$C_{20}$-alkyl. Cycloalkyl preferably represents mono-, bi- or tricyclic $C_3$-$C_{10}$-cycloalkyl, in particular cyclopentyl and cyclohexyl. Possible substituents for the alkyl and cycloalkyl radicals are, for example: halogen, such as Cl, Br, or F, CN, $OCOR^{10}$, $OR^7$, $COOR^{10}$, $SR^7$, $CONR^8R^9$ and $OCON^8R^9$, wherein $R^7$ to $R^{10}$ have the meanings given below.

Aralkyl ($R^1$ to $R^4$) in particular represents phenyl- or naphthyl-$C_1$-$C_4$-alkyl, it being possible for the aryl radicals to be substituted, for example as described below for aryl.

Aryl ($R^1$ to $R^4$) preferably represents those carbocyclic-aromatic radicals which contain 1, 2, 3 or 4, in particular 1 or 2, rings, such as phenyl, diphenyl and naphthyl.

Hetaryl radicals ($R^1$ to $R^4$) are preferably those heterocyclic (aromatic) radicals which contain 1, 2, 3 or 4, in particular 1 or 2, five-, six- or seven-membered rings, at least one of which contains 1, 2 or 3, preferably 1 or 2, heteroatoms from the series comprising O, N and S. Examples of heterocyclic radicals which may be mentioned are:

pyridyl, pyrimidyl, pyrazinyl, triazinyl, furoyl, pyrolyl, thiophenyl, quinolyl, coumarinyl, benzofuranyl, benzimidazolyl, benzoxazolyl, dibenzofuranyl, benzothiophenyl, dibenzothiophenyl, indolyl, carbazolyl, pyrazolyl, imidazolyl, oxazolyl, isoxazolyl, thiazolyl, indazolyl, benzothiazolyl, pyridazinyl, quinnolyl, quinazolyl, quinoxalyl, phthalazinyl, phthalazindionyl, phthalamidyl, chromonyl, naphtholactamyl, quinolonyl, ortho-sulphobenzoic acid-imidyl, maleimidyl, naphtharidinyl, benzimidazolonyl, benzoxazolonyl, benzothiazolonyl, benzothiazothionyl, quinazolonyl, quinoxalonyl, phthalazonyl, dioxopyrimidinyl, pyridonyl, isoquinolonyl, isoquinolinyl, isothiazolyl, benzisoxazolyl, benzisothiazolyl, indazolonyl, acridinyl, acridonyl, quinazolindionyl, quinoxalindionyl, benzoxazindionyl, benzoxazinonyl and naphthalimidyl The aryl and hetaryl radicals can be substituted, for example, by halogen, such as chlorine, bromine and fluorine, —CN, $R^6$, $OR^7$, $SR^7$, $NR^8R^9$, $COOR^{10}$, $COR^{10}$, $NR^8COR^{10}$, $NR^8COOR^{10}$, $NR^8CONR^8R^9$, $NHSO_2R^{10}$, $SO_2R^{10}$, $SO^2OR^{10}$, $CONR^8R^9$, $SO_2NR^8R^9$, $N=N-R^{11}$, $OCOR^{10}$ and $OCONR^8R^9$.

$R^6$ designates optionally substituted alkyl, preferably $C_1$-$C_{18}$-alkyl, in particular $C_1$-$C_4$-alkyl, or optionally substituted cycloalkyl, preferably $C_3$-$C_7$-cycloalkyl, in particular cyclohexyl or cyclopentyl.

Possible substituents on the alkyl and cycloalkyl radicals $R^6$ are, for example: halogen, such as Cl, Br and F, CN, $OCOR^{10}$, $OR^7$, $COOR^{10}$, $SR^7$, $CONR^8R^9$ and $OCONR^8R^9$.

$R^7$, $R^8$ and $R^9$ designate hydrogen, optionally substituted alkyl, in particular $C_1$-$C_{18}$-alkyl, preferably $C_1$-$C_4$-alkyl, optionally substituted cycloalkyl, in particular cyclohexyl or cyclopentyl, optionally substituted aralkyl, in particular phenyl- or naphthyl-$C_1$-$C_4$-alkyl, optionally substituted aryl, in particular phenyl or naphthyl, or an optionally substituted heterocyclic radical, in particular the radical of a 5- or 6-membered heterocyclic ring having 1, 2 or 3 heteroatoms from the series comprising O, N and S, on to which a benzene ring can be fused.

The alkyl and cycloalkyl radicals $R^7$, $R^8$ and $R^9$ can be substituted, for example, by Cl, Br, F, CN, mono-$C_1$-$C_4$-alkylamino, di-$C_1$-$C_4$-alkylamino, phenyl or naphthyl, which can be substituted by Cl, Br, F, $C_1$-$C_6$-alkyl or $C_1$-$C_6$-alkoxy, or by heterocyclic radicals of a 5- or 6-membered heterocyclic ring system having 1 or 2 heteroatoms from the series comprising O, N and S, on to which a benzene ring can be fused.

$R^8$ and $R^9$ together, including the N atom, can also form a 5- or 6-membered heterocyclic ring, for example a morpholine, piperidine or phthalimide ring. The aryl and aralkyl radicals $R^8$ and $R^9$ can be substituted, for example, by Cl, Br, F, $C_1$-$C_{18}$-alkyl, preferably $C_1$-$C_4$-alkyl or by $C_1$-$C_{18}$-alkoxy, preferably $C_1$-$C_4$-alkoxy.

$R^{10}$ designates hydrogen, optionally substituted alkyl, in particular $C_1C_{18}$-alkyl, preferably $C_1$-$C_4$-alkyl, optionally substituted cycloalkyl, in particular cyclopentyl or cyclohexyl, optionally substituted aralkyl, in particular phenyl- or naphthyl-$C_1$-$C_4$-alkyl, preferably benzyl, or optionally substituted aryl, in particular phenyl or naphthyl.

The radicals mentioned for $R^{10}$ can be substituted in the same was as the corresponding radicals $R^8$ and $R^9$.

$R^{11}$ designates the radical of a coupling component, preferably a coupling component of the benzene, naphthalene, acetoacetatearylide, pyrazole or pyridone series, or a phenyl radical which is optionally substituted by Cl, Br, F, $C_1$-$C_{18}$-alkyl, preferably $C_1$-$C_4$-alkyl or by $C_1$-$C_{18}$-alkoxy, preferably $C_1$-$C_4$-alkoxy.

Cat represents, for example, an alkali metal cation or alkaline earth metal cation or a transition metal cation, such as copper and nickel cations, or $NHR_7R_8R_9$, wherein $R^7$—$R^9$ have the abovementioned meaning and preferably represent H or optionally substituted alkyl.

Preferred compounds in the context of the formula (Ia/Ib) are those of the formula

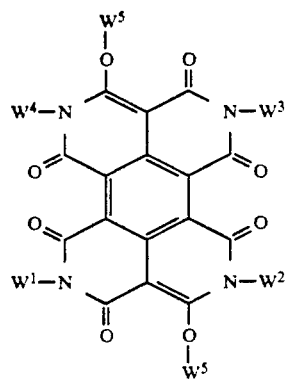
(Ic)

or

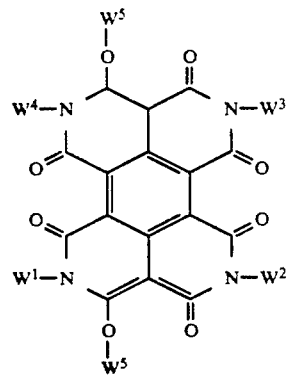
(Id)

wherein $W^1$ to $W^4$ denote optionally substituted alkyl- or cycloalkyl and $W^5$ denotes hydrogen or optionally substituted alkyl- or cycloalkyl or Cat.

Particularly preferred compounds of the formula (Ic/Id) are those in which $W^1$ to $W^4$ denote unsubstituted $C_1$-$C_{20}$-alkyl and $W^5$ denotes hydrogen, an optionally substituted ammonium ion or a metal cation.

Especially preferred compounds (Ia/Ib) are those of the formula

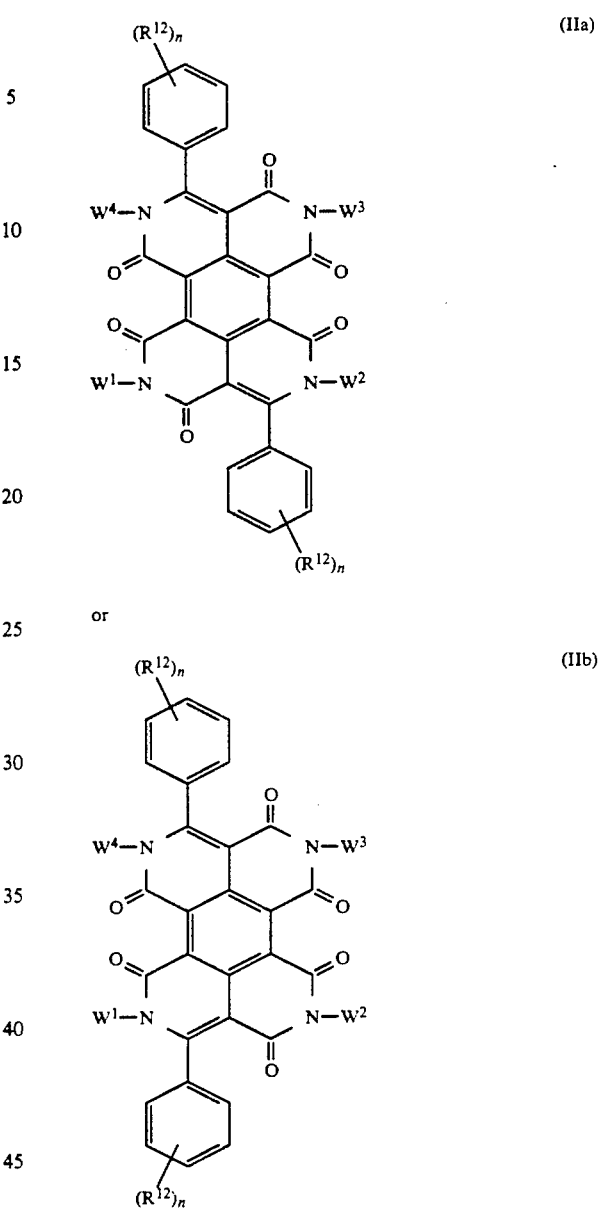

wherein
$W^1$ to $W^4$ have the abovementioned meanings and
$R^{12}$ can be Cl, Br, F, CN, $R^6$, $OR^7$, $SR^7$, $NR^8R^9$, $COOR^{10}$, $COR^{10}$, $NR^8COR^{10}$, $NR^8COOR^{10}$, $NR^8CONR^8R^9$, $NHSO_2R^{10}$, $SO_2R^{10}$, $SO_2OR^{10}$, $CONR^8R^9$, $SOOCOR^{10}$ or $OCONR^8R^9$ with the abovementioned substituents meanings for $R^6$ to $R^{10}$ and n can be 0–3.

The oxidation, described in J. Chem. Soc. 1960, page 3513 et seq, of

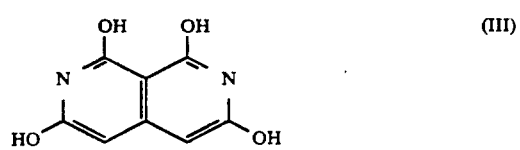
(III)

gives a pentacyclic compound of the probable structure

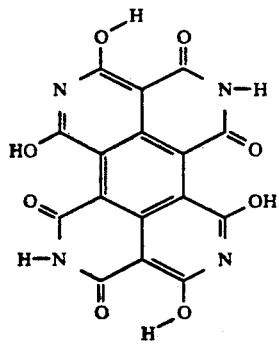
(IVa)

or

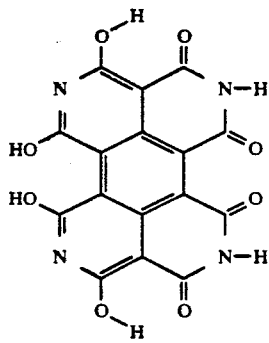
(IVb)

or of one of the possible tautomers with the symmetry of IVa ($C_{2h}$) or IVb ($C_{2v}$), for example

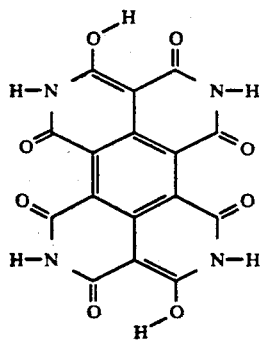
(IVc)

or salts thereof.

The compounds Ia or Ib in which at least one of the radicals $R^1$ to $R^4$ represents alkyl, cycloalkyl or aralkyl are obtained starting from the compounds IVa or IVb, in particular di-alkali metal salts or di-alkaline earth metal salts thereof, by reaction with alkylating agents at about 150° to 250° C., preferably 180° to 220° C., if appropriate under pressure and in the presence of inert solvents.

Examples of suitable akylating agents are alkyl halides, sulphonic acid alkyl esters or sulphuric acid alkyl esters.

Compounds (Ia/Ib) having various degrees of alkylation can thus be obtained, depending on the amount of alkylating agent, the temperature and the duration of the reaction.

Thus, for example, a large excess of methyl tosylate gives a tetra-N-methyl compound of the formula

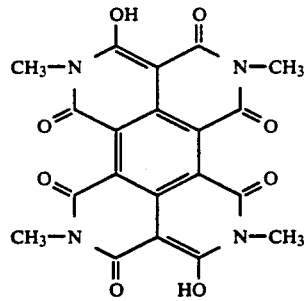
(Va)

or

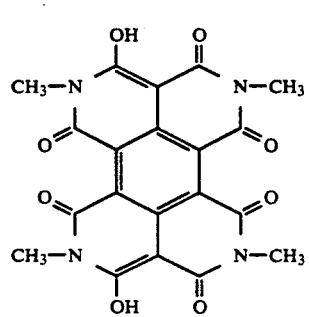
(Vb)

The compounds Ic or Id where $W^1$ to $W^4$=alkyl can be used as pigments for surface coatings or pigmenting plastics or as soluble dyestuffs for colouring plastics, depending on the chain length of the alkyl groups.

The compounds of the formula Ic/Id are obtained in a form suitable for use as pigments or can be converted into a suitable form by after-treatment processes which are known per se, for example by dissolving or swelling in strong inorganic acids, such as sulphuric acid, and pouring the mixture on to ice. The fine division can also be achieved by grinding with or without grinding auxiliaries, such as inorganic salts or sand, if appropriate in the presence of solvents, such as toluene, xylene, dichlorobenzene or N-methylpyrrolidone. The tinctorial strength and transparency of the pigment can be influenced by varying the after-treatment.

On the basis of their fastness to light and migration, the compounds of the formula Ic/Id are suitable for the most diverse pigment applications. They can thus be used for the preparation of very fast pigmented systems as a mixture with other substances, formulations, paints, printing inks, coloured paper and coloured macromolecular substances. A mixture with other substances can be understood as meaning, for example, those with inorganic white pigments, such as titanium dioxide (rutile) or with cement. Formulations are, for example, flush pastes with organic liquids or pastes or fine pastes with water, dispersing agents and if appropriate preservatives. The term paint represents, for example, surface coatings which dry by physical means or oxidation, stoving enamels, reaction surface coatings, two-component surface coatings, emulsion paints for weatherproof coatings and distempers.

Printing inks are to be understood as those for printing paper, textiles and sheet metal. The macromolecular substances can be of natural origin, such as rubber, obtained by chemical modification, such as acetyl cellulose, cellulose butyrate or viscose, or produced synthetically, such as polymerizates, polyaddition products and polycondensates. Substances which may be mentioned are plastic compositions, such as polyvinyl chloride, polyvinyl acetate, polyvinyl propionate, polyolefins, for example polyethylene, or polyamides, high molecular weight polyamides, polymerizates and copolymerizates of acrylic esters, methacrylic esters, acrylonitrile, acrylamide, butadiene and styrene and polyurethanes and polycarbonates. The substances pigmented with the products claimed can also be in any desired form.

Compounds Ic/Id where $W^5$ = Cat and $W^1$ to $W^4$ = alkyl are obtained from the corresponding compounds where $W^5$ = H by reaction with the corresponding metal hydroxides, metal chlorides or metal salts of carboxylic acids or the corresponding ammonium compounds or amines at elevated temperature (20° to 200° C.), if appropriate in the presence of dipolar aprotic solvents, such as dimethylformamide or dimethylsulphoxide.

If appropriate, the starting substance is first reacted with stoichiometric amounts of NaOH to give the disodium salt, and this is then subjected to a metal exchange reaction. The Ni, Cu and Ca derivatives thus obtained are blue pigments which are very fast to light.

Compounds of the formula

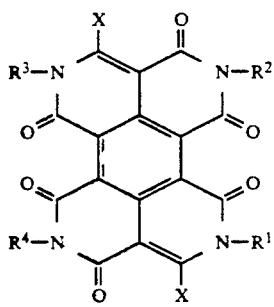

(VIa)

or

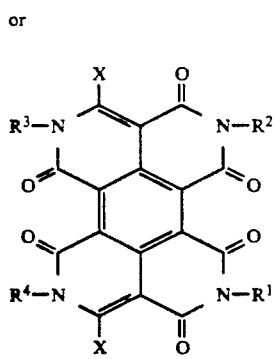

(VIb)

where $R^1$ to $R^4$ = alkyl, cycloalkyl or aralkyl and X = halogen are obtained from the corresponding compounds where X = OH by reaction with halogenating agents, for example $PCl_5$, $PBr_5$ or $POCl_3$, at about 120° to 200° C., preferably at 130° to 180° C., if appropriate in the presence of inert solvents, such as nitrobenzene or dichlorobenzene. The compounds VIa or VIb are orangecoloured sparingly soluble solids.

Compounds of the formula

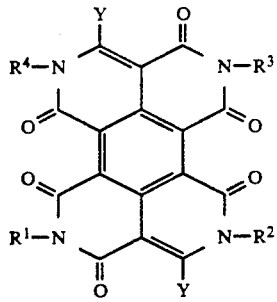

(VIIa)

or

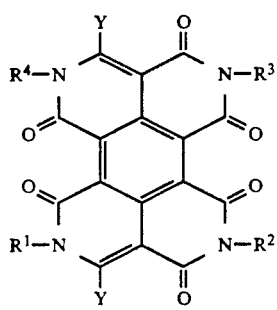

(VIIb)

where $Y = NR^1R^2, SR^1$ or $OR^1$, are obtained by reaction of VIa/VIb where X = halogen with nucleophiles Y-H (VIII) at temperatures of about 20° to 200° C., preferably 40° to 140° C., if appropriate in an inert solvent and in the presence of acid-binding agents, such as alkali metal carbonates, bicarbonates or acetates. $R^1$ and $R^2$ have the abovementioned meanings.

Examples of suitable compounds VIII are ammonia, optionally substituted aromatic or aliphatic amines, alcohols, phenols or thiophenols or mercaptans or salts thereof. If alcoholates, phenolates or thiophenolates are used, the corresponding alcohols are the preferred solvent. Compounds of the formula

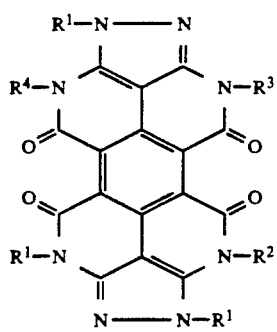

(IXa)

or

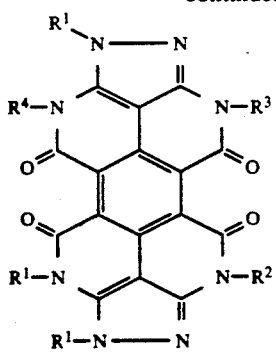

are obtained by reaction of VIa/VIb (X=halogen) with hydrazines of the formula $$R_1NH-NH_2 \quad (X)$$

wherein $R^1$ has the abovementioned meaning, at about 100° to 200° C., preferably 140° to 180° C., if appropriate in the presence of inert solvents and acid-binding agents.

The compounds IXa/IXb are blue to green pigments. Compounds of the formula

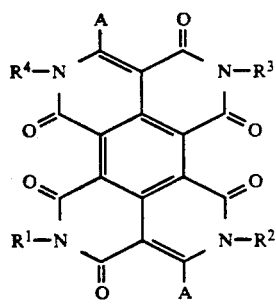

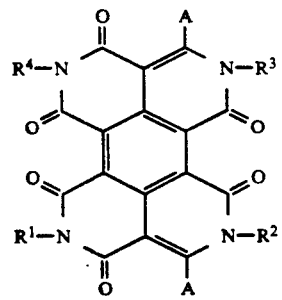

are obtained by reaction of VIa/VIb, where X=halogen, with aromatic compounds of the formula $$A-H \quad (XII)$$

wherein A denotes an optionally substituted aryl or hetaryl radical, for example those such as are described for $R^1$ to $R^4$, in the presence of Friedel-Crafts catalysts.

In general, an excess of XII and more than the equimolar amounts of the catalyst, for example AlCl$_3$, are employed and the reaction is carried out at about 100° to 200° C., if appropriate in the presence of an inert solvent. The mixture is worked up in the customary manner.

The compounds XIa/XIb can also be prepared from VIa/VIb (X=halogen) and organometallic compounds, for example phenylmagnesium bromide, in inert solvents.

XIa/XIb are pigments or soluble dyestuffs depending on the radical A.

EXAMPLE 1

26 g of the dry disodium salts of IV a/b are stirred in 90 ml of methyl toluene sulphonate at an internal temperature of 190° C. for 12.5 hours. During this procedure, 45 ml of o-dichlorobenzene are gradually added to improve the stirrability of the reaction mixture.

After 12.5 hours, the mixture is cooled to 100° C., 150 ml of methanol are then added and the mixture is stirred until cold. The solid is filtered off with suction at room temperature and the material on the suction filter is stirred in water, filtered off again with suction and dried. 23 g of a compound of the formula (XIIIa)

(XIIIb)

are obtained as a red-violet pigment with very good fastnesses to overcoating and migration properties.

IR data: 2965, 1710, 1695, 1600, 1420, 1375, 1325, 1255, 1180, 1070, 1005, 830, 790 cm$^{-1}$ $^{13}$C-NMR data (Solid CPMAS)

δ=28.5 (N—CH$_3$), 82.3 (C-3), 122.6 (C-5, C-5'), 129.4 (C-4), 158.9 (C-6, C-6'), 165.1 ppm (C-2, C-2')

If the corresponding amounts of octyl, hexadecyl or menthyl tosylate are used, soluble dyestuffs with which, for example, polystyrene can be coloured blue are obtained.

EXAMPLE 2

5 g of the compound XIII are stirred together with 5.7 g of Ni(OAc)$_2$·4H$_2$O in 30 parts of dimethylformamide at 100° to 110° C. for 80 minutes. The product is then filtered off with suction and washed with methanol. 5.9 g of a blue pigment which has excellent fastnesses to overcoating and light are obtained.

EXAMPLE 3

5 g of the compound XIII are stirred in 100 ml of an approximately 2% strength aqueous NH: solution at room temperature for 24 hours. After the product has been filtered off with suction, 4.4 g of a blue pigment which has similar properties to that described in Example 2 are obtained.

According to the solid $^{13}$C-NMR spectrum, the compound XIII is present in this salt as the dianion of the formula

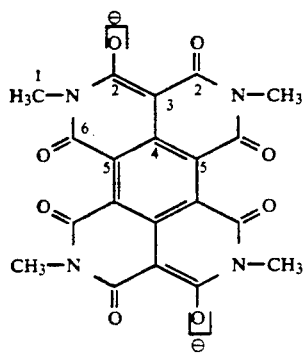

(XIIIb)

or

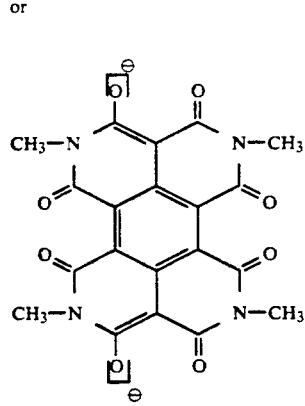

$^{13}$C-NMR data: δ=25.1 (C-1), 84.5 (C-3), 115.2, 116.2 (C-5, C-5'), 128.7 (C-4), 159.1, 159.5 (C-2, C-2'), 161.0 ppm (C-6, C-6').

EXAMPLE 4

11.8 g of the compound XIII are stirred together with 10.9 g of Pcl$_5$ in 250 ml of nitrobenzene at 110° to 120° C. for 5.5 hours. After this time, a further 2.0 ml of Pcl$_5$ are subsequently added and the mixture is stirred at the abovementioned temperature for another 2 hours. The product is then filtered off with suction at 65° C. and washed with nitrobenzene. The suction filter cake is stirred into 200 ml of methanol and filtered off with suction again. 11.3 g of an orange-coloured solid of the formula

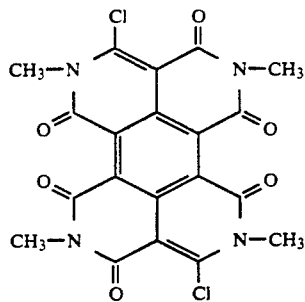

(XIVa)

or

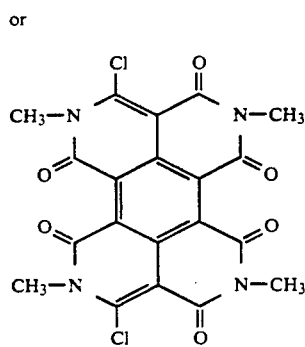

(XIVb)

are obtained
UV/VISλ=490 nm (ε=5450)
IR:γ=1715, 1660, 1550, 1510, 1475, 1330, 1290, 1080 cm$^{-1}$

EXAMPLE 5

20 g of XIV are stirred together with 13 g of 4-chloroaniline and 12 ml of triethylamine in 250 ml of nitrobenzene at 110° to 120° C. for 5 hours.

After the mixture has been cooled to room temperature and 300 ml of methanol have been added, the product is filtered off with suction and washed thoroughly with methanol in order to remove the triethylamine hydrochloride. 22 g of the compound of the formula

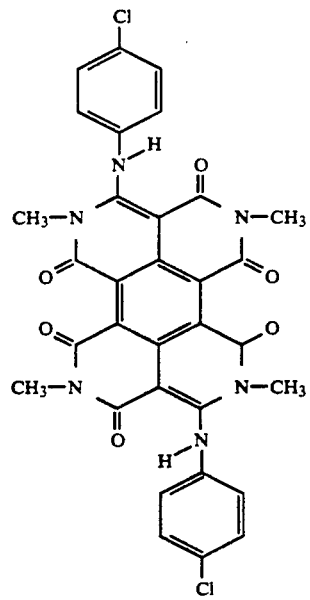

or

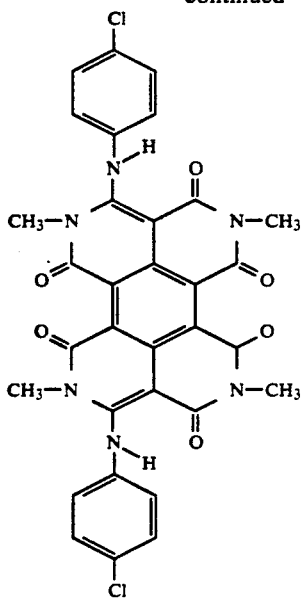

are obtained.

IR data: γ=1700, 1630, 1605, 1580, 1490, 1445, 1120, 1100, 795 cm$^{-1}$ $\lambda_{max}$=581 nm The compounds of the following table can be prepared analogously to Example 5 by reaction with the nucleophiles R—H:

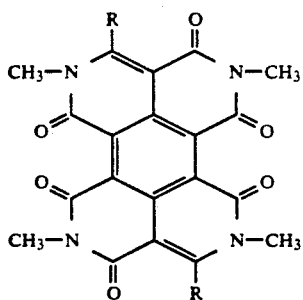

and

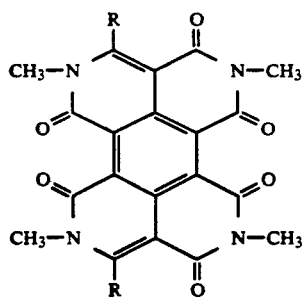

| Example | R | Colour shade | λmax [nm] | Remarks |
|---|---|---|---|---|
| 5 | Cl-⟨⟩-NH— | blue | 581 | soluble dyestuff |
| 6 | ⟨⟩-NH— | blue | 586 | soluble dyestuff |
| 7 | pyrazolyl | orange | 478 | soluble dyestuff |
| 8 | imidazolyl | orange | 483 | soluble dyestuff |
| 9 | ⟨⟩-S- | red | 524 | soluble dyestuff |
| 10 | t-Bu-⟨⟩-NH— | blue | 588 | soluble dyestuff |
| 11 | ⟨⟩-O— | red | 480 | soluble dyestuff |

EXAMPLE 12

20 g of XIV are mixed with 13 g of aluminium chloride and suspended in 90 ml of N,N-diethylaniline. The suspension is heated to 180° C. and stirred at this temperature for 5 hours. It is then cooled and stirred with 500 ml of ethanol, the solid is filtered off with suction and suspended in 50 ml of water and the suspension is acidified slightly with dilute hydrochloric acid. After filtration with suction, washing until neutral and drying, 25 g of an orange-coloured pigment of the formula

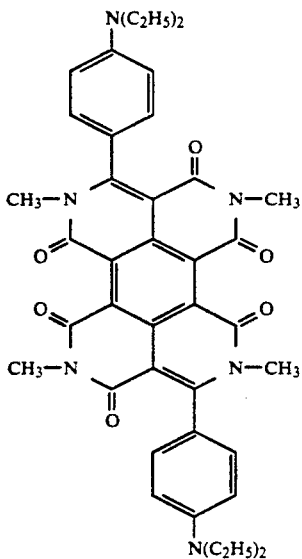

or

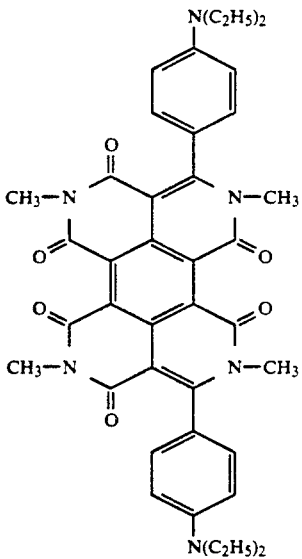

are obtained.

EXAMPLE 13

0.2 g of pigment according to Example 1 is mixed with 100 g of polyethylene, polypropylene or polystyrene granules. The mixture can either be injection moulded at 220° to 280° C. directly in an injection moulding machine or processed to coloured glass in an extruder or to coloured milled sheets on a mixing mill. The bars or milled sheets are granulated, if appropriate, and injection moulded in an injection moulding machine.

The red-violet shaped articles have a very good fastness to light and migration. Synthetic polyamides of caprolactam or adipic acid and hexamethylenediamine or the condensates of terephthalic acid and ethylene glycol can be coloured in a similar manner at 280° to 300° C., if appropriate under a nitrogen atmosphere.

EXAMPLE 14

4 g of finely ground pigment according to Example 1 are dispersed in 92 g of a stoving enamel of the following composition:

33% of alkyd resin
15% of melamine resin
5% of glycol monomethyl ether
34% of xylene
13% of butanol Products based on synthetic and vegetable fatty acids, such as coconut oil, castor oil, ricinene oil, linseed oil and the like are suitable alkyd resins. Instead of melamine resins, urea resins can be used. After the dispersion has taken place, the pigmented surface coating is applied to foils of paper, glass, plastic or metal and stoved at 130° C. for 30 minutes. The coatings have very good resistance to light and weather and a good fastness to overcoating.

This stoving enamel is brushed on to white paper and stoved at 130° C. and displays a red-violet colour shade.

I claim:

1. Heterocyclic compounds of the formula

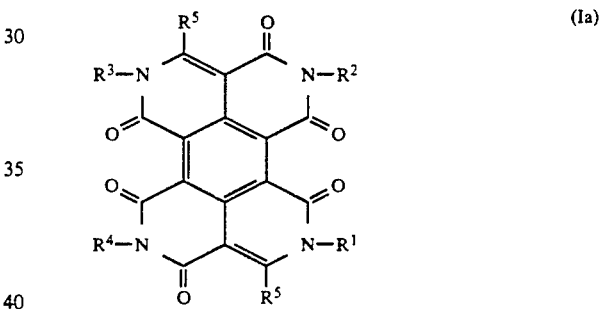

or

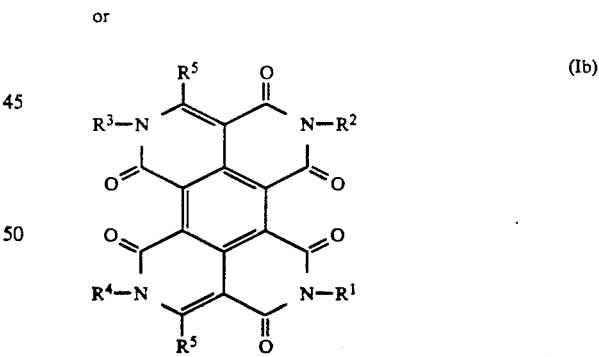

wherein:

$R^1$, $R^2$, $R^3$ and $R^4$ denote H, alkyl, cycloalkyl, aralkyl, aryl or heterocyclic aromatic radicals, which contain 1, 2, 3 or 4 five-, six- or seven-membered rings, at least one of which contains 1, 2 or 3 heteroatoms from the series comprising O, N and S, denotes halogen $NR^1R^2$, $SR^1$, $OR^1$, aryl, pyrazolyl, imidazolyl or OCat, wherein Cat = a cation, and wherein, for $R^1$ to $R^4$=H, $R^5$ does not represent OH or ONa.

2. Compounds of claim 1, of the formula

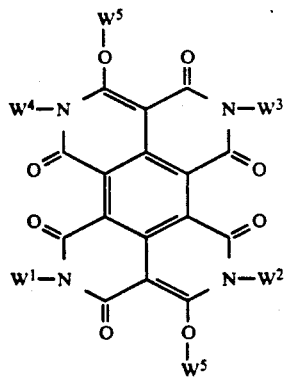
(Ic)

or

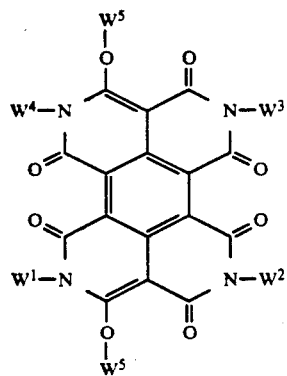
(Id)

wherein $W^1$ to $W^4$ denote optionally substituted alkyl- or cycloalkyl and $W^5$ denotes hydrogen or optionally substituted alkyl- or cycloalkyl or Cat.

3. Compounds of claim 2, where $W^1$ to $W^4$ denote unsubstituted $C_1$-$C_{20}$-alkyl and $W^5$ denotes hydrogen, an optionally substituted ammonium ion or a metal cation.

4. Compounds of claim 1, of the formula

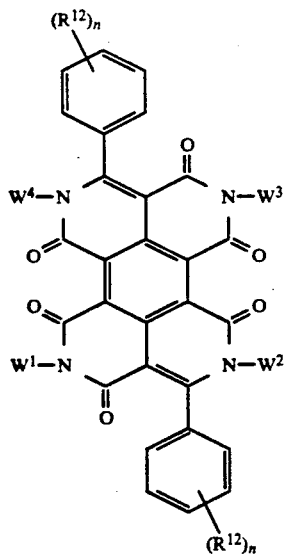
(IIa)

or

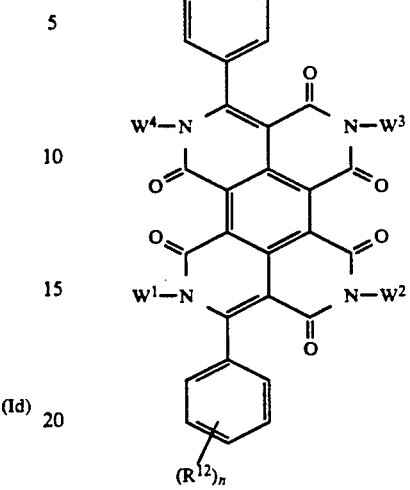
(IIb)

$W^1$ to $W^4$ have the meanings given in claim 3 and $R^{12}$=Cl, Br, F, CN, $R^6$, $OR^7$, $SR^7$, $NR^8R^9$, $COOR^{10}$, $COR^{10}$, $NR^8COR^{10}$, $NR^8COOR^{10}$, $NR^8CONR^8R^9$, $NHSO_2R^{10}$, $SO_2R^{10}$, $SO_2OR^{10}$, $CONR^8R^9$, $SOOCOR^{10}$ or $OCONOR^8R^9$ with the abovementioned substituent meanings for $R^6$ to $R^{10}$ and n=0−3, wherein $R_6$ denotes optionally substituted alkyl or cycloalkyl, $R_7$-$R_9$ denotes an optionally substituted alkyl, cycloalkyl, aralkyl, aryl or heterocylic radical with a five- or six-membered heterocyclic ring having 1,2 or 3 heteroatoms from the series comprising O, N and S, on to which a benzene ring can be fused, wherein $R_8$ and $R_9$, together with the N atom, can form a 5- or 6-membered heterocyclic ring, and $R^{10}$ deonotes H or optionally substituted alkyl, cycloalkyl, aralkyl or aryl.

5. Compounds of the formula

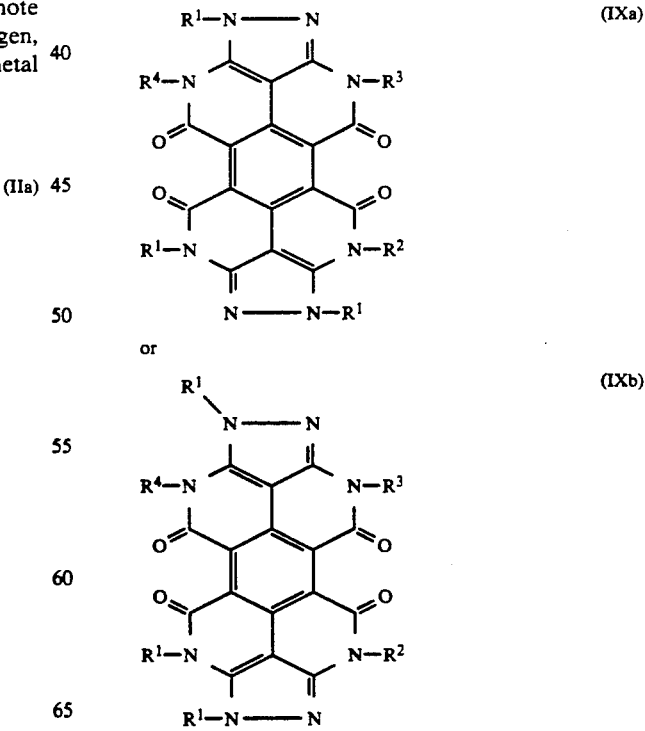

wherein $R_1$-$R_4$ have the meaning given in claim 1.

* * * * *

UNITED STATES PATENT AND TRADEMARK OFFICE
CERTIFICATE OF CORRECTION

PATENT NO. : 5,097,027

DATED : March 17, 1992

INVENTOR(S) : Hochstetter, Hans

It is certified that error appears in the above-identified patent and that said Letters Patent is hereby corrected as shown below:

Col. 16, line 63    Before " denotes " insert -- $R^5$ --

Col. 18, line 27    Delete " $OCONOR^8R^9$ " and substitute -- $OCONR^8R^9$ --

Signed and Sealed this

Twenty-first Day of September, 1993

Attest:

BRUCE LEHMAN

*Attesting Officer*       *Commissioner of Patents and Trademarks*